(12) United States Patent
Mackool et al.

(10) Patent No.: US 11,432,960 B1
(45) Date of Patent: Sep. 6, 2022

(54) OPHTHALMIC MEDICAL INSTRUMENT WITH ILLUMINATED SNARE

(71) Applicant: Accuvision Designs, LLC, Farmingdale, NY (US)

(72) Inventors: Richard James Mackool, Sarasota, FL (US); Christopher Dean Smith, Ronkonkoma, NY (US); Evan Rittenhouse Jones, Levittown, NY (US); Richard Jonathan Mackool, Pelham, NY (US)

(73) Assignee: Accuvision Designs, LLC, Farmingdale, NY (US)

( * ) Notice: Subject to any disclaimer, the term of this patent is extended or adjusted under 35 U.S.C. 154(b) by 0 days.

(21) Appl. No.: 17/590,081

(22) Filed: Feb. 1, 2022

(51) Int. Cl.
*A61F 9/007* (2006.01)

(52) U.S. Cl.
CPC ................. *A61F 9/00736* (2013.01)

(58) Field of Classification Search
CPC .......... A61F 9/00754; A61B 90/30; A61B 2090/306; A61B 2090/309; A61B 17/32056; A61B 2017/00907
See application file for complete search history.

(56) References Cited

U.S. PATENT DOCUMENTS

| 9,775,743 | B2 | 10/2017 | Clauson et al. |
| 10,485,700 | B1* | 11/2019 | MacKool ............... A61B 90/30 |
| 10,603,212 | B2 | 3/2020 | MacKool |
| 2011/0135259 | A1* | 6/2011 | Guenter ............. G02B 6/02342 385/103 |
| 2012/0035425 | A1* | 2/2012 | Schaller ............ B29C 45/14622 600/249 |
| 2013/0110090 | A1* | 5/2013 | Nguyen ............. A61B 17/2909 606/1 |
| 2015/0282888 | A1 | 10/2015 | Olson |
| 2016/0074220 | A1* | 3/2016 | Ianchulev ............... A61B 17/32 606/107 |
| 2017/0325394 | A1 | 11/2017 | Clement et al. |
| 2018/0338767 | A1* | 11/2018 | Dasnurkar ....... A61B 17/12172 |
| 2021/0161711 | A1 | 6/2021 | MacKool et al. |

* cited by examiner

*Primary Examiner* — Richard G Louis
*Assistant Examiner* — Chima U Igboko
(74) *Attorney, Agent, or Firm* — Collard & Roe, P.C.

(57) ABSTRACT

An ophthalmic surgical instrument for severing a lens of an eye has an elongated shaft and a snare formed by a wire extending along the elongated shaft and having a looped segment that moves between contracted and dilated configurations. When the shaft is inserted through the pupil and the looped segment is placed around the lens, the bottom portion of the looped segment engages and severs a bottom portion of the lens upon moving toward the contracted configuration. A light-conducting element extends along at least a portion of a length of the looped segment, and a light source is in communication with the light-conducting element, such that light from the light source travels through the element and illuminates at least a portion of the length of the looped segment. The light-conducting element can be a tube surrounding the wire, or can be a solid filament extending adjacent the wire.

14 Claims, 10 Drawing Sheets

OPHTHALMIC MEDICAL INSTRUMENT WITH ILLUMINATED SNARE

BACKGROUND OF THE INVENTION

1. Field of the Invention

This invention relates to an ophthalmic medical instrument containing a snare for bisecting a patient's lens to facilitate removal during cataract surgery. In particular, the invention relates to a medical instrument having a snare that is illuminated via a light conducting tube that surrounds the snare.

2. The Prior Art

Snare devices have been used to bisect a patient's lens during cataract surgery, in order to facilitate removal of the lens. The device has generally taken the form of an elongated shaft with a wire extending out or near a distal end of the shaft. The wire is in form of a loop that is placed around the lens and then contracted, so that the wire severs the lens and allows the severed lens to be removed from the surrounding lens capsule more easily. One of the problems with the traditional snare devices is that the surgeon cannot see the wire behind the lens, so accurate placement is difficult, and can complicate the surgery. One attempt to make the wire snare more visible is described in U.S. Pat. No. 10,485,700 to Mackool, the disclosure of which his herein incorporated by reference. In that device, the wire is constructed to be hollow and a light source is in communication with the lumen of the wire. An aperture in the wire at a point located behind the lens allows the light to escape. The light can be seen through the lens to identify the location of the wire to the surgeon.

One drawback to this configuration is that manufacturing and assembling the wire with the light source is expensive and cumbersome. In addition, the wire must be made larger to accommodate the lumen, and is thus less effective in severing the lens during use. As these devices are generally not re-used, it would be desirable to provide a device for severing a lens that is simple and inexpensive to manufacture as well as effective and reliable during use.

SUMMARY OF THE INVENTION

It is therefore an object of the invention to provide an ophthalmic device for severing a lens, in which the wire forming the snare is not required to be hollow. This object is accomplished by an ophthalmic surgical instrument for severing a lens of an eye, comprising an elongated shaft having a distal end portion, and a snare formed by a wire extending along the elongated shaft and having a looped segment disposed adjacent the distal end portion and being configured to move between a contracted configuration and a dilated configuration, in which the looped segment assumes a diameter approximating the diameter and shape of a lens of an eye. When the elongated shaft is inserted through the pupil and the looped segment is placed around the lens, the bottom portion of the looped segment is configured to engage and sever a bottom portion of the lens upon moving toward the contracted configuration. This enables the surgeon to more easily remove the lens during surgery.

In order to enable the surgeon to visualize the looped segment after it is placed around the lens, the device according to the invention also comprise a light-conducting element adjacent at least a portion of a length of the looped segment, and a light source in communication with the light-conducting element, such that light from the light source travels through the element and illuminates at least a portion of the length of the looped segment. The light from the light source travels through the material of the element and exits out a distal end of the element, which can be located at any point along the looped segment but preferably at a place located behind the lens during surgery and preferably at a center of the lens. The point at which the light exits the end of the element forms a bright spot that can be seen through the lens during cataract surgery, so that proper positioning of the snare formed by the looped segment is ensured.

In one embodiment, the light-conducting element is in the form of a solid filament that runs adjacent the wire.

In another embodiment, the light-conducting element is in the form of a tube that surrounds the wire. The tubular structure surrounding the wire creates a greater surface area for light emission as compared to a single strand, thus increasing the visibility of the snare during use.

In a further embodiment, the entire light-conducting element is translucent or transparent, so that the light exits along the length of the element as well, illuminating the entire extent of the looped segment. In this situation, the light-conducting element may extend along an entire length of the looped segment, so that the entire snare is illuminated during surgery. In this embodiment wherein the element tube, the tube is constructed to have a small enough diameter so it can still function to sever the lens during contraction of the wire.

The light-conducting element is preferably made of polyurethane, but any other suitable transparent, translucent or opaque flexible material that scatters light could be used.

In another embodiment, the light conducting element and wire can be covered by an opaque covering so that light from the light source is only visible at an end of the element. In this embodiment, the end of the light-conducting element should be positioned behind the lens during surgery, as this the only area where the light is visible. It is also possible to provide openings along the length of the covering for additional bright spots if desired.

The opaque covering can be made of metal, plastic or any other suitable material. The covering could be woven, braided, coiled, painted or laminated or in any suitable configuration that would allow for movement of the tube and wire during contraction and dilation.

The wire is preferably made of nitinol, which has shape memory capabilities so that an oval shape of the looped segment is maintained throughout use. Other suitable materials could also be used. In one embodiment, the looped portion of the wire has a bend at a bottom of the loop. If the light-conducting element terminates at the bend, the end of the light-conducting element faces toward the shaft, and thus light exiting from the light-conducing element is directed through the lens and back toward the surgeon for maximum visibility.

In a preferred embodiment, the instrument includes a housing connected to the elongated shaft. The housing has an actuator connected to the wire and is configured to move the wire between the contracted and dilated configurations. Preferably, the light source is disposed in the housing and the light-conducting element extends through the elongated shaft into the housing where it is connected to the light source. In another embodiment, the light source is located external to the housing and the light-conducting element extends through the housing and out of the housing to the external light source.

The actuator can take on any suitable form. In one embodiment, the actuator is formed by a sliding element disposed in a slot in the housing. Sliding the sliding element in a direction away from the distal end of the elongated shaft moves the wire into the contracted position, causing the wire to sever the lens, and sliding the sliding element toward the distal end of the elongated shaft moves the wire into the dilated position where it is ready for use.

The light source could be formed by any suitable light source, such as a light-emitting diode (LED). If the light source is disposed in the housing, it is preferably powered by a battery disposed in the housing, so that the instrument is portable and does not require a wired connection to a power source. Alternatively, the light source could be located remote from the surgical instrument, and the tube could extend through the instrument to the light source.

BRIEF DESCRIPTION OF THE DRAWINGS

Other objects and features of the present invention will become apparent from the following detailed description considered in connection with the accompanying drawings. It is to be understood, however, that the drawings are designed as an illustration only and not as a definition of the limits of the invention.

In the drawings, wherein similar reference characters denote similar elements throughout the several views.

DETAILED DESCRIPTION OF THE PREFERRED EMBODIMENTS

Figure 1:
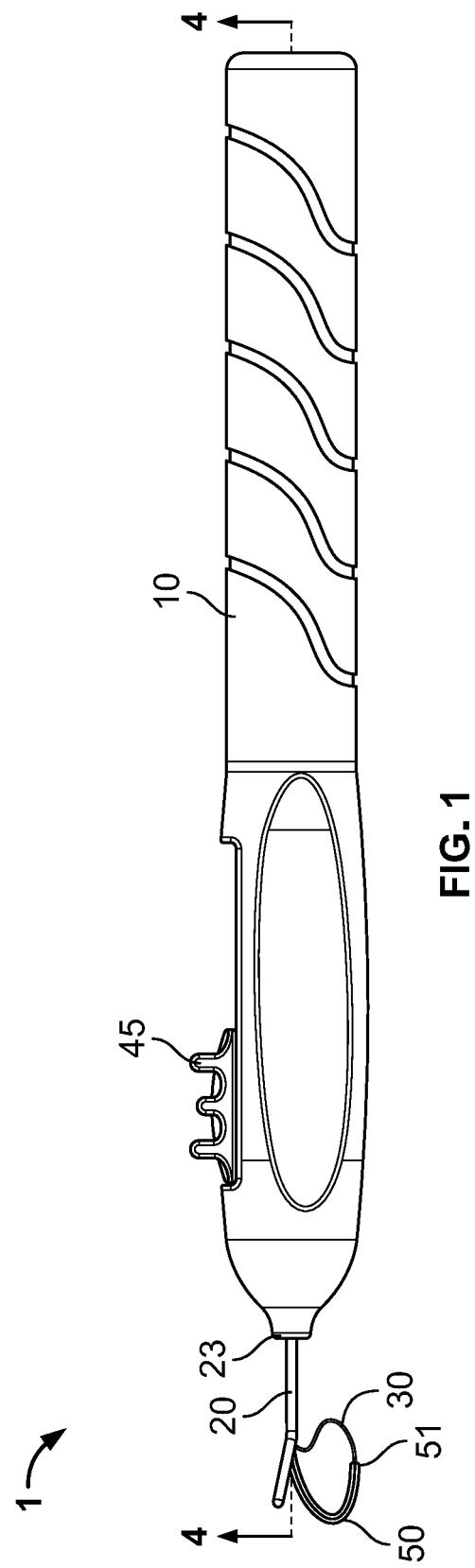
FIG. 1 shows a side view of the ophthalmic surgical instrument according to the invention.
Figure 2:
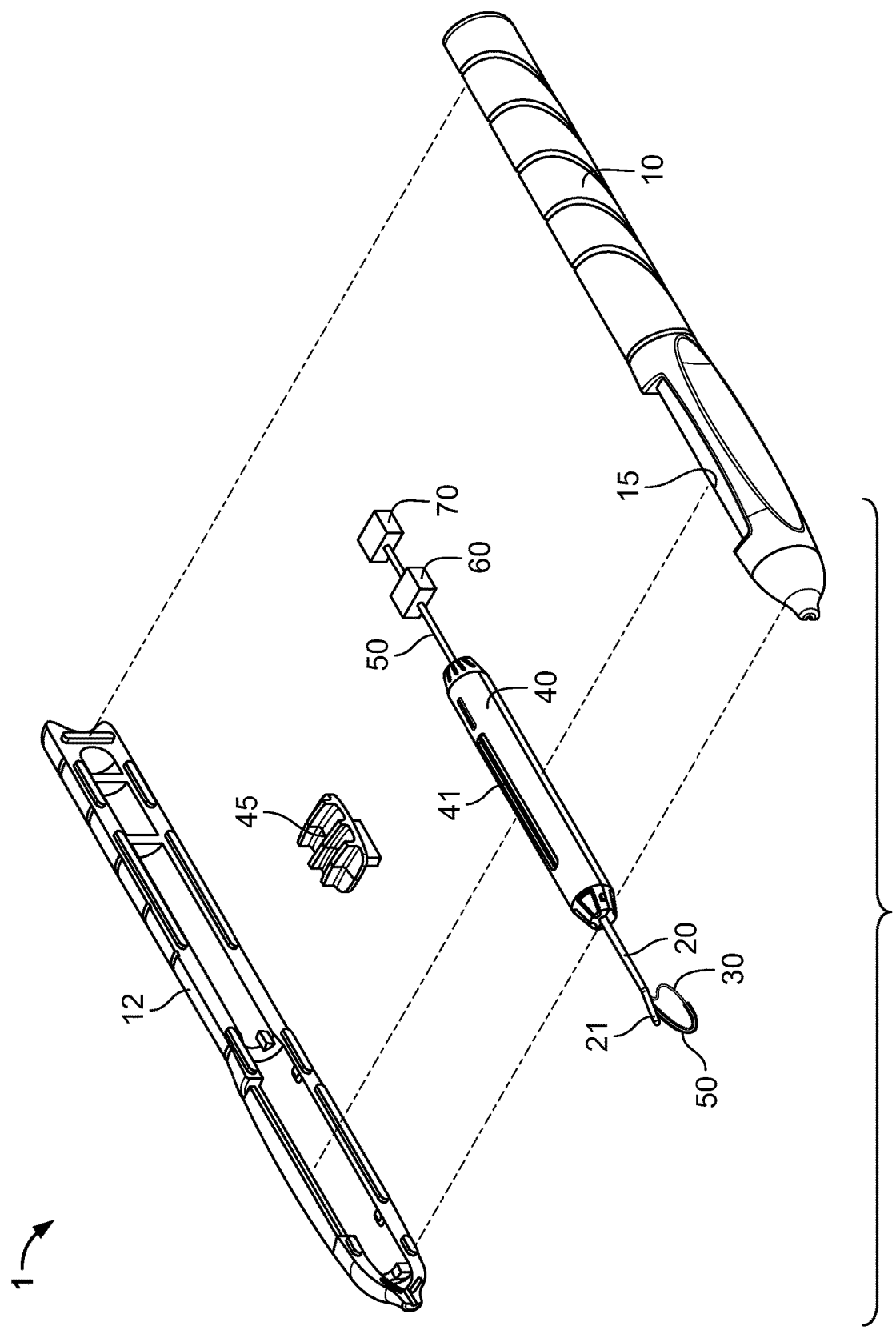
FIG. 2 shows the instrument with the housing cover removed.
Figure 3:
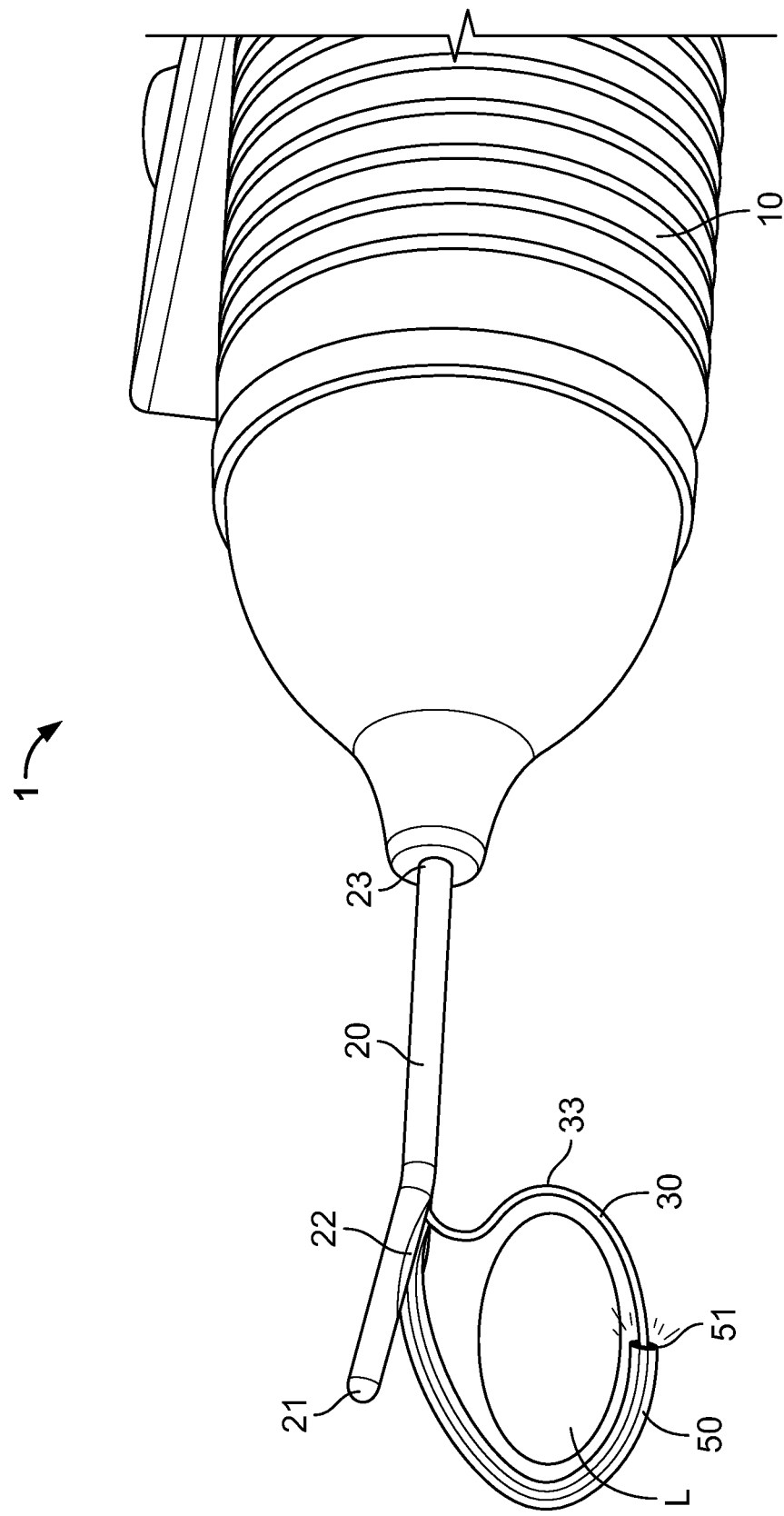
FIG. 3 shows an exploded view of the instrument.

Turning to the drawings, FIGS. 1-3 show an ophthalmic surgical instrument 1 that has a housing 10, an elongated shaft in the form of a needle 20 having a distal end 21, an opening 22 in a side wall thereof, and a snare 30 formed by a wire, for severing lenticular tissue. The elongated shaft 20 is dimensioned for passage through a corneal incision and has a proximal end portion 23 that may be integrally formed with or attached to the housing 10 or to a slider cartridge 40 shown in FIG. 2.

Figure 4:
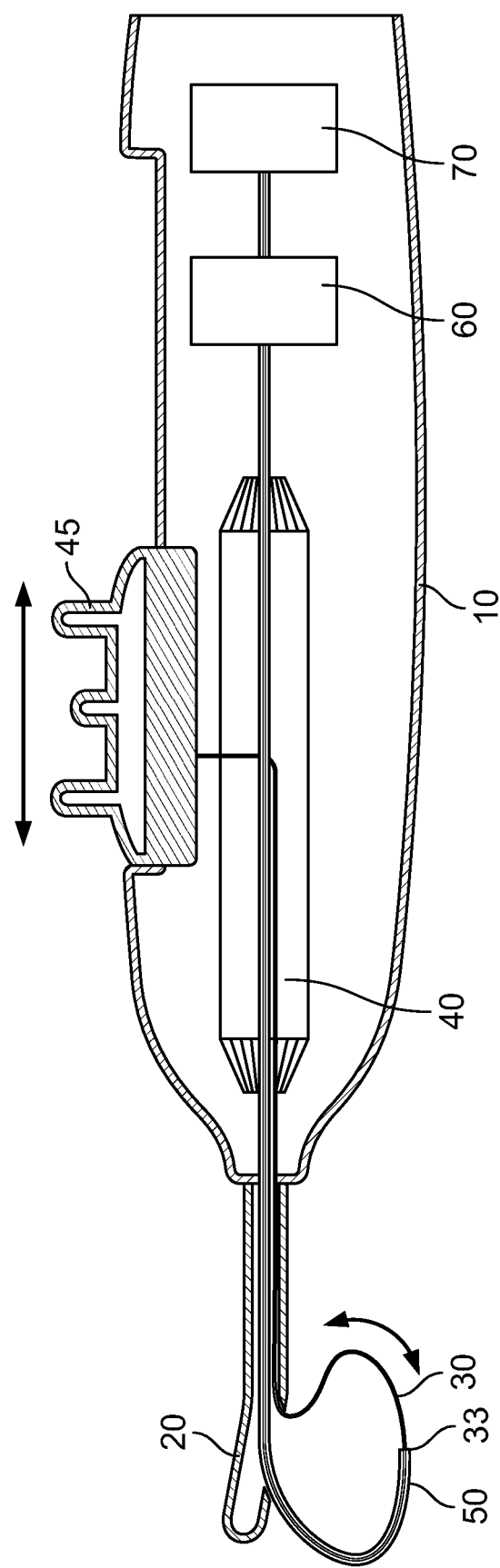
FIG. 4 shows a cross-sectional view of the instrument along lines IV-IV of FIG. 1.

The snare 30 of the ophthalmic surgical instrument 1 is movable relative to and within the elongated shaft 20 via an actuation mechanism formed by slider cartridge 40 and slider button 45, which rests in channel 41 of slider cartridge 40. Slider cartridge 40 is accessible through an opening 15 in housing 10, A first end of snare 30 is connected to slider button 45, as shown in FIG. 4, and the second end of snare 30 is fixed within the housing, so that moving slider button 45 along channel 41 expands and retracts looped segment 33 formed by snare 30. Retracting looped segment 33 by sliding button 45 away from distal end 22 allows snare 30 to bisect a lens that is disposed within loop 33 during surgery.

The snare 30 is fabricated from a pliable, metal material, such as, for example, nickel-titanium or any other suitable superelastic material. The snare may be fabricated from any suitable ductile material. Surrounding the snare 30 is a light-conducting tube 50, which extends at least partially around the looped segment 33. In the embodiment of FIGS. 1-4, tube 50 terminates at a distal end 51, which is located at a bottom of the looped segment 33. As shown in FIG. 4, tube 50 extends around the top portion of looped segment 33, enters the elongated shaft 20 with snare 30, extends through slider cartridge 40, and connects to a light source 60, which is disposed in housing 10. Light source 60 can be connected to power source 70, such as a battery, also disposed in housing 10, so that the ophthalmic surgical instrument 1 is completely portable and wireless.

The light source 60 may be a light-emitting diode (LED), a compact fluorescent lamp, an incandescent light bulb, or any other suitable source of light. The light source 60 is in communication with the tube 50 so that the light from the light source is emitted out of the tube and out of distal end 51. Tube 50 is also preferably made of a flexible, translucent material such as polyurethane, so that the light is emitted along the length of the tube 50 and is visible along the entire length. In this embodiment, the light would appear as a bright spot at the distal end 51 exit as well. In another embodiment, Tube 50 is made of an opaque material, or is covered by an opaque coating or covering, so that only the light exiting out of distal end 51 is visible. In one embodiment, tube 50 can be covered by a metal covering.

In use, the elongated shaft 20 is inserted through a corneal incision and a capsulorhexis to position the distal end portion 21 around a surface of the lens L. The surgeon is able to use the light emitted from the tube 50 appropriately position the snare 30 relative to the lens "L." With the looped segment 33 in the selected position, which is verified using the light transmitted out of the bottom 51 of tube 50, the looped segment 33 is transitioned from the dilated configuration to the contracted configuration, thereby severing the lens "L."

Figure 5:
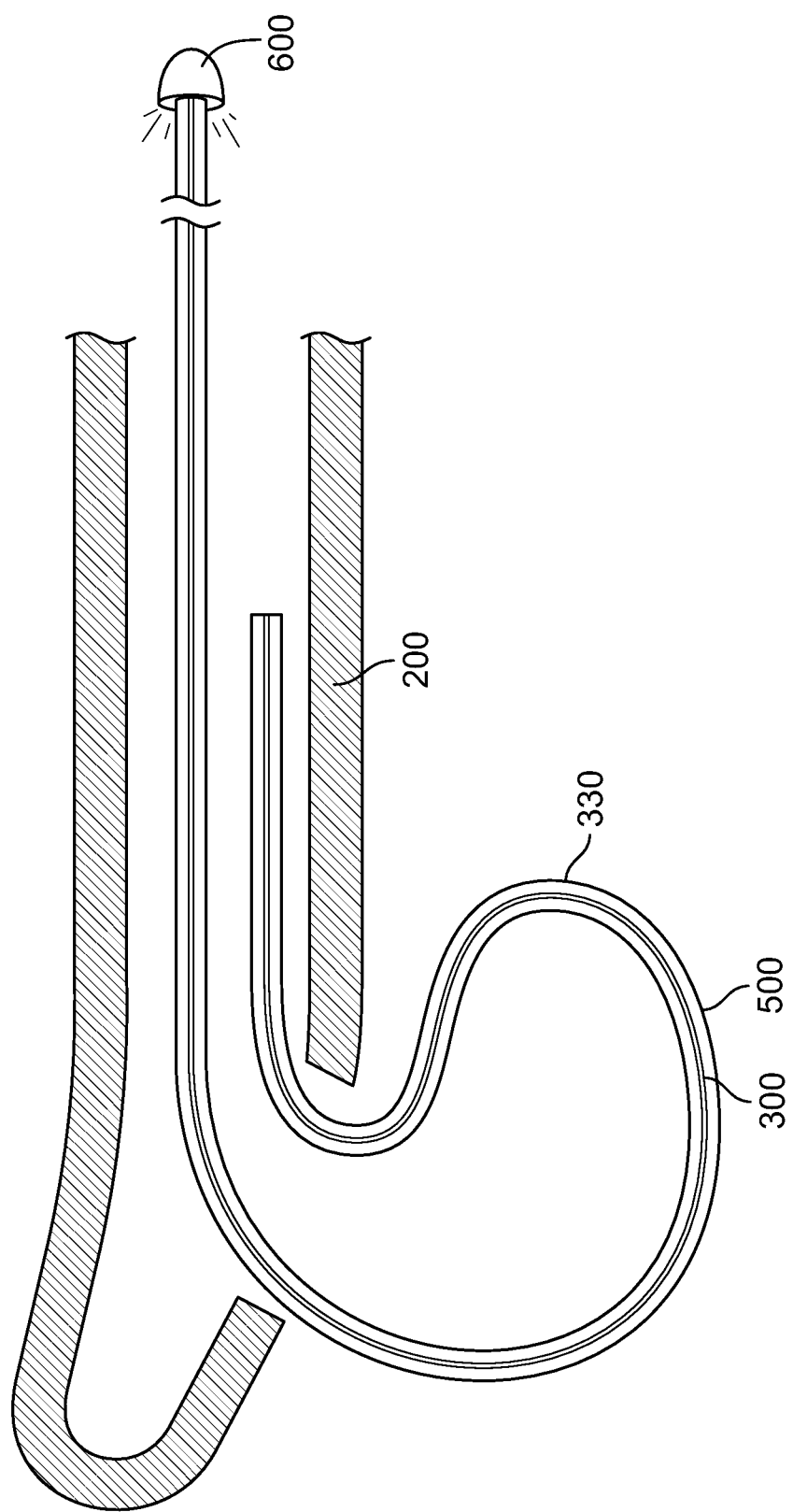
FIG. 5 shows an alternative embodiment of the snare.

FIG. 5 shows an alternative embodiment of the invention, where device 100 has an elongated shaft 200 with an opening 220 through which a snare 300 formed by wire extends in a looped segment 330. Snare 300 is completely encased in a light-conducting tube 500, which is connected to a light source 600, in the same manner as described above with respect to FIGS. 1-4. Tube 500 is transparent or translucent, so that the light from light source 600 is visible along the entire extent of the snare. Tube 500 is thin enough so that snare 300 surrounded by tube 500 is still able to bisect a lens when snare 300 is moved to the retracted position in the manner described above with respect to FIGS. 1-4 (using the same slider mechanism as described above).

Figure 6:
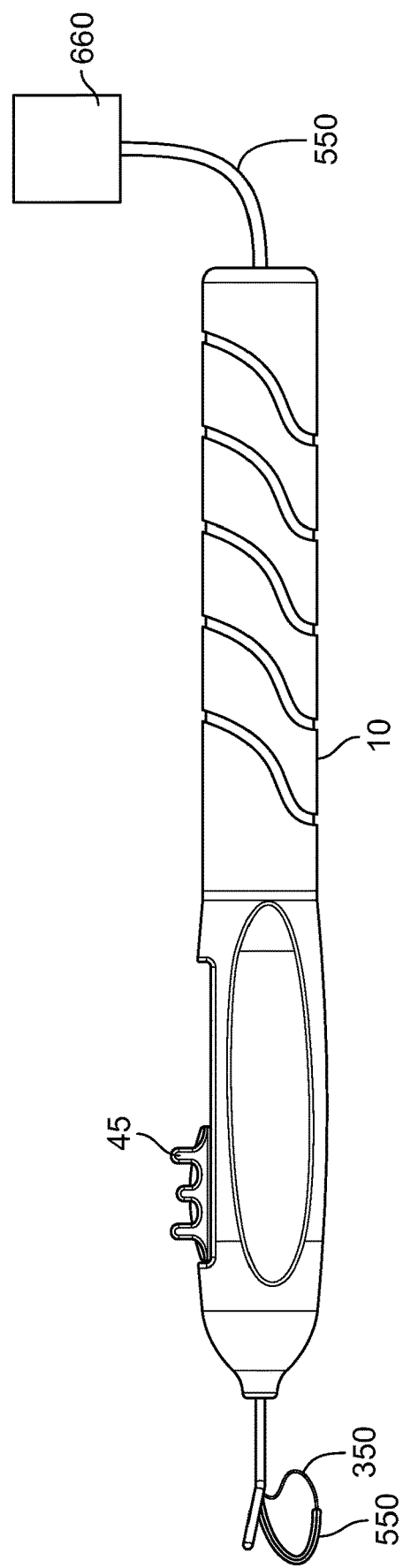
FIG. 6 shows an alternative embodiment of the instrument, with an external light source.

FIG. 6 shows another alternative embodiment, where light source 660 is located outside the housing 10 of ophthalmic surgical instrument 1. Snare 350 surrounded by tube 550 extends entirely through the housing and out to remote light source 660, which can be located on a remote device or by itself. This embodiment allows for the use of a larger, more powerful light source and a larger power supply than may be available to place inside housing 10.

Figure 7:
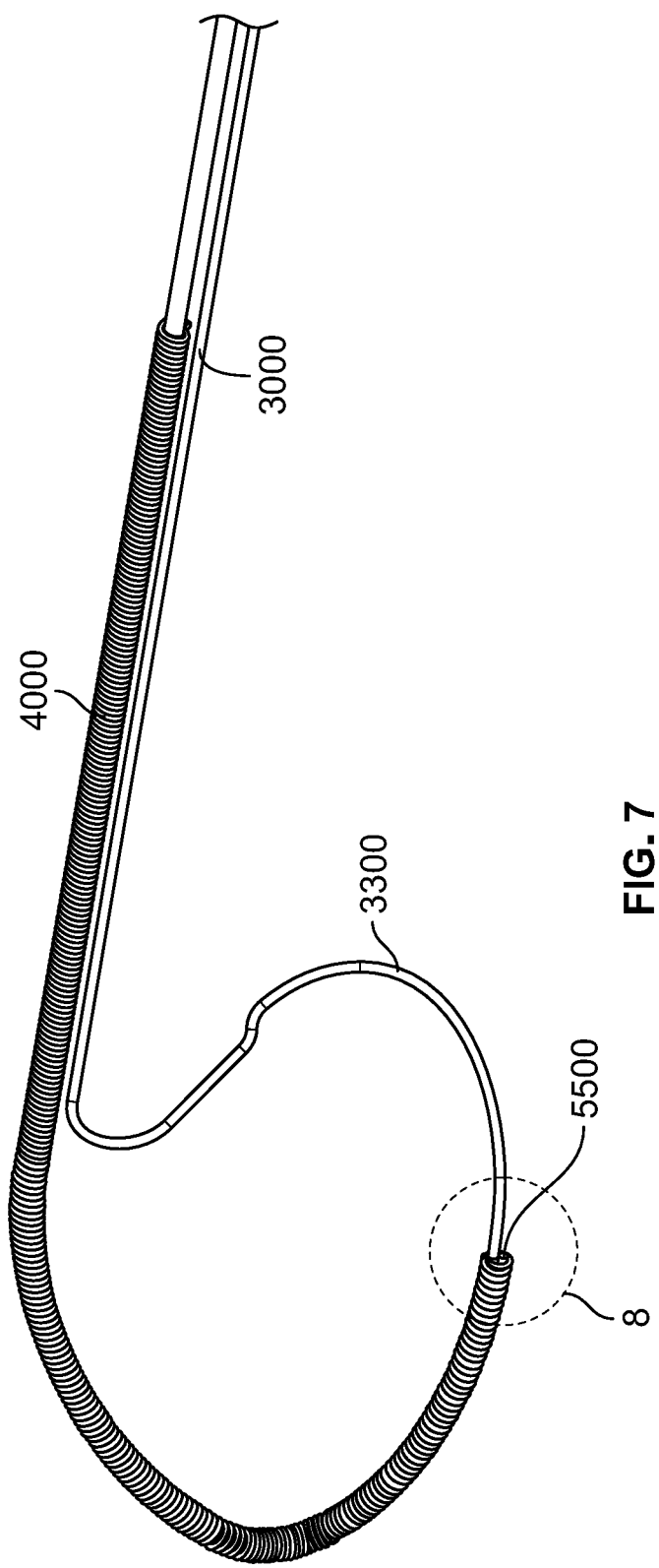
FIG. 7 shows another alternative embodiment of the invention.
Figure 8:
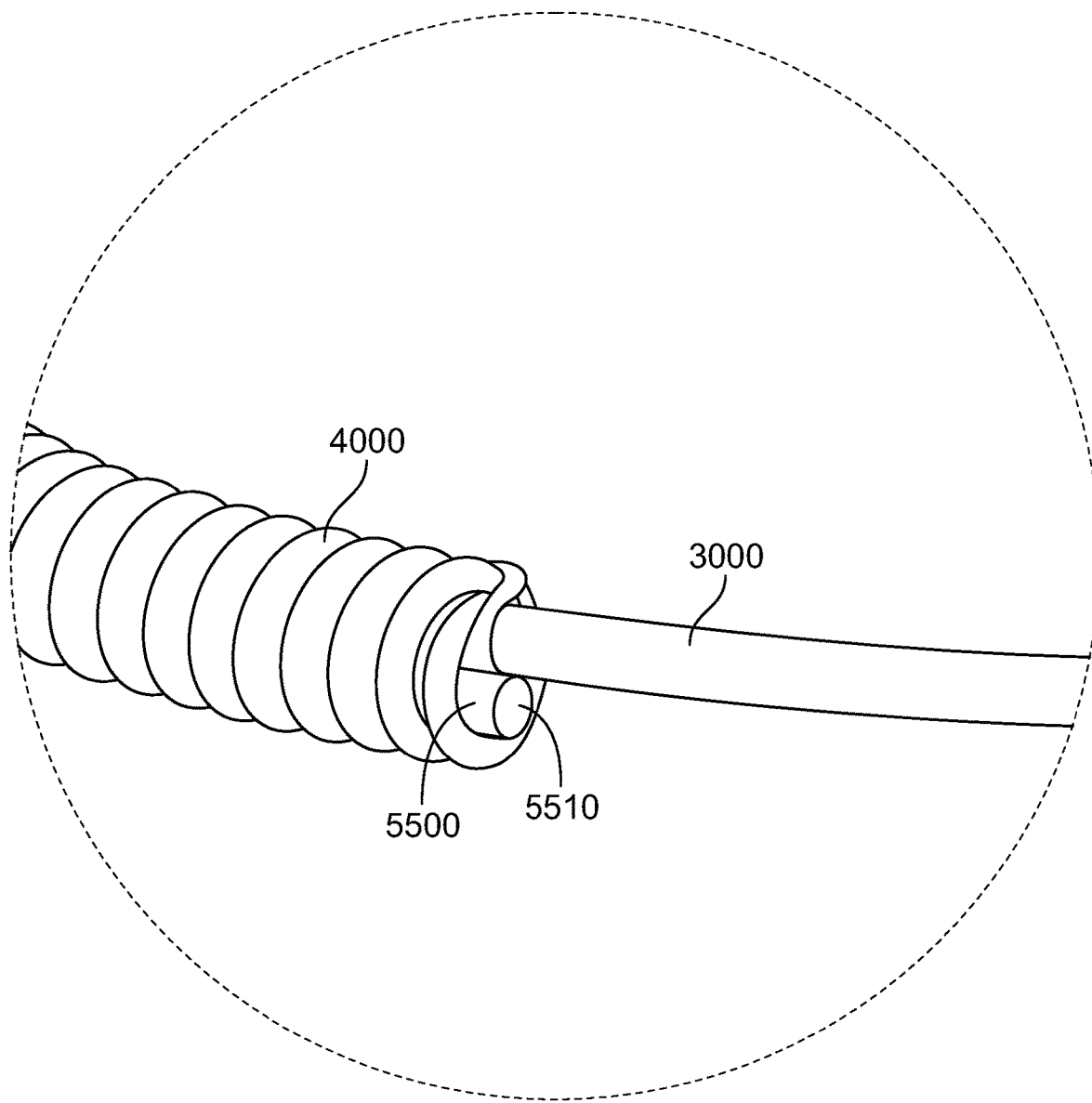
FIG. 8 shows an enlarged view of circle 8 in FIG. 7.

An alternative embodiment of the invention is shown in FIGS. 7 and 8. Here, a light-conducting element in the form of a solid filament 5500 extends parallel to snare 3000, and terminates at a mid-point of looped segment 3300 of snare 3000. A coiled cover 4400 surrounds the snare 3000 and filament 5500 to keep the two components together. Cover 4400 can be formed of metal wire or any other suitable material, such as a polymer, or any other suitable mixture of materials. In this embodiment, the light from filament 5500 exits out of end 5510 and forms a bright spot behind the lens during surgery, in the same manner as explained above with respect to FIGS. 1-4. Filament 5500 is connected to a light source that is disposed in the housing 10 or in a location remote from housing 10 in the same manner as disclosed with the embodiments of FIGS. 1-6.

Figure 9:
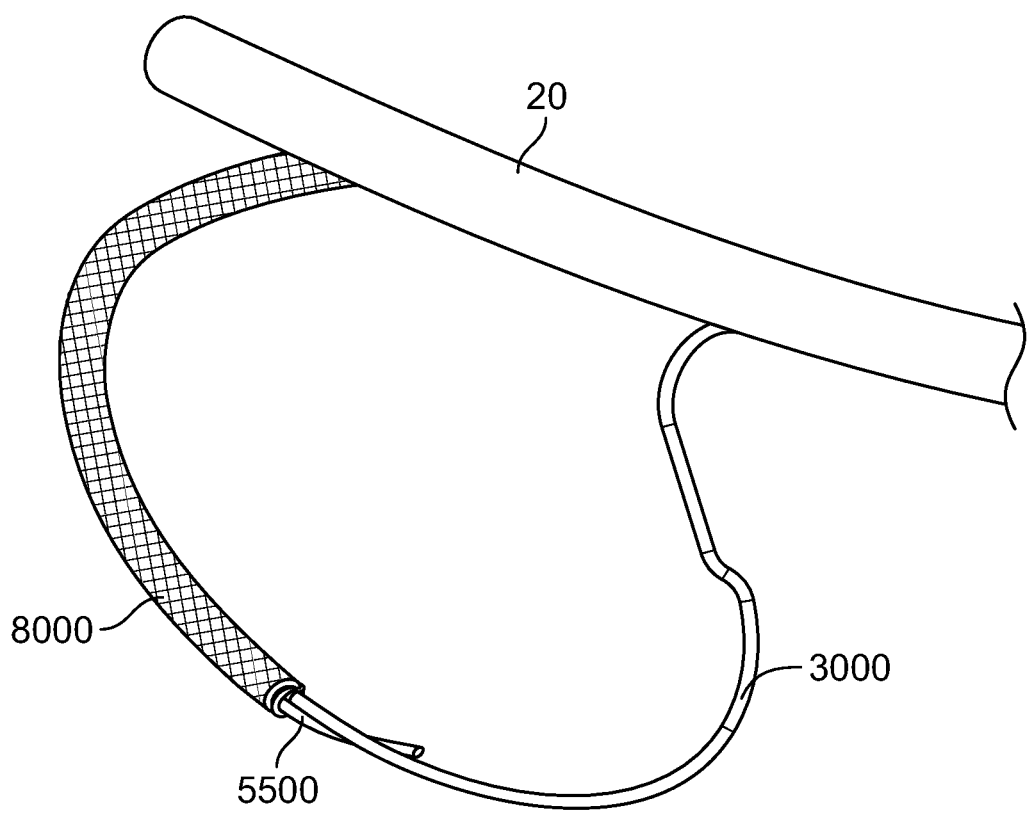
FIG. 9 shows another alternative embodiment of the invention.

FIG. 9 shows a further embodiment of the invention, which is identical to the embodiment of FIGS. 7 and 8, using the instrument of FIGS. 1-6, except that in this situation, cover 8000 is in the form of a woven material, typically a metallic tape or thread, but any other suitable materials could be used as well. It is also envisioned that a cover could be constructed of a solid tube or a molded material that covers both the snare 3000 and the filament 5500.

Figure 10:
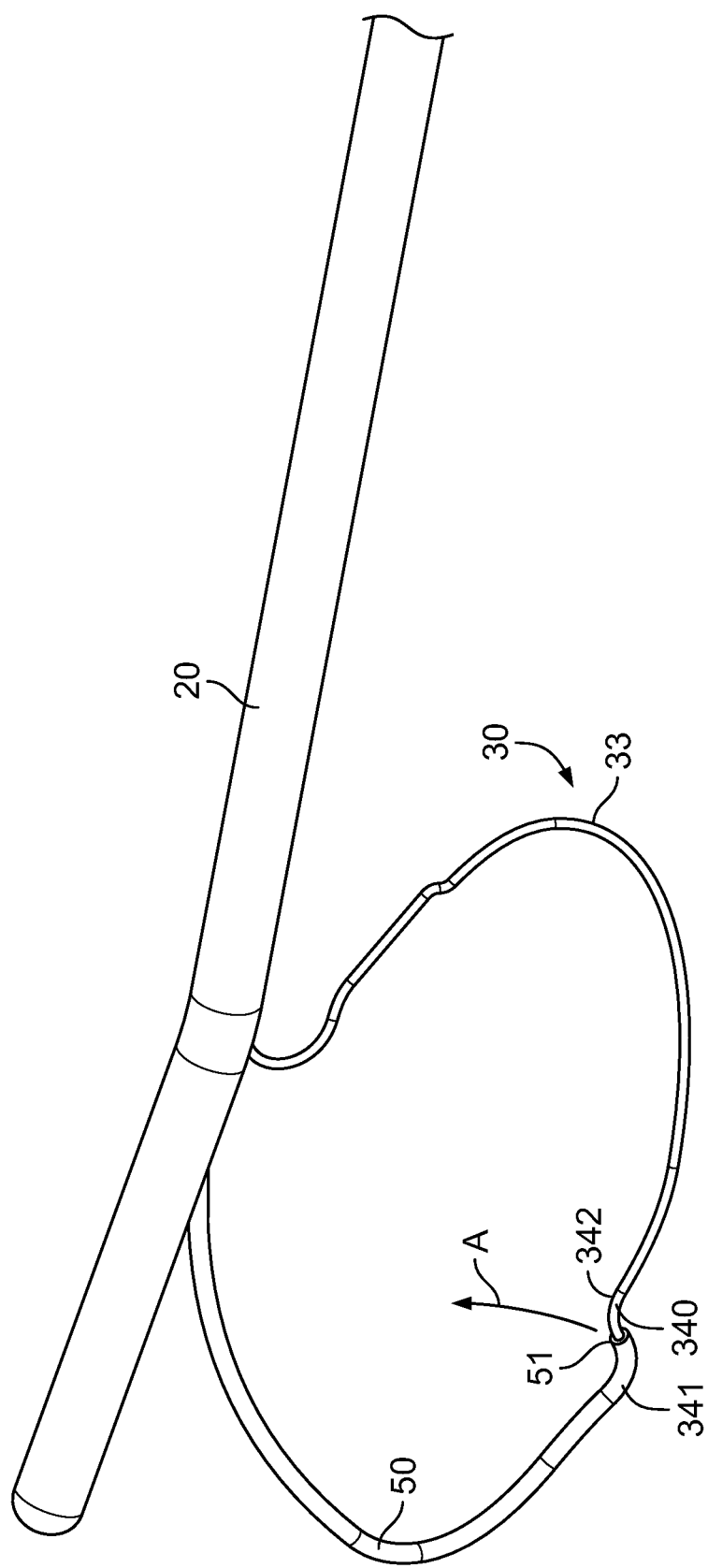
FIG. 10 shows a further embodiment of the invention.

A further embodiment is shown in FIG. 10, here the ophthalmic surgical instrument 1 is identical to the instrument shown in FIGS. 1-4, except that here, snare 30 is bent in two places in opposite directions at a bottom of looped portion 33, in the form of a Z- or S-shape, so that an intermediate section 340 between bends 341 and 342 extends upward toward elongated shaft 20, obliquely to the extent of looped portion 33. Tube 50 terminates in the intermediate section 340, so that distal end 51 is aimed toward elongated shaft 20. Thus, the bright spot formed by the light exiting tube 50 is aimed toward the surgeon during surgery (along arrow A), and is thus more visible, even when viewed through a lens that is substantially opaque with a cataract. The snare of FIG. 10 could also be used in an embodiment where the light-conducting element is in the form of a solid filament such as shown by filament 5500 in FIGS. 7-9. In either case, the end of the light-conducting element is aimed back toward the elongated shaft 20, so that the brightest part of the apparatus is aimed at the surgeon, thus making the snare more visible behind the lens. The light-conducting element could be covered or coated so that the light is only visible at end 51, such as shown in the embodiment of FIGS. 7-9, or can be uncovered so that light is visible along the extent of the light-conducting element, i.e., tube 50.

Accordingly, while only a few embodiments of the present invention have been shown and described, it is obvious that many changes and modifications may be made thereunto without departing from the spirit and scope of the invention.

What is claimed is:

1. An ophthalmic surgical instrument for severing a lens of an eye, comprising:
an elongated shaft having a distal end portion;
a wire extending along the elongated shaft and having a looped segment disposed adjacent the distal end portion and being configured to move between a contracted configuration and a dilated configuration, in which the looped segment assumes a diameter approximating the a diameter and shape of a lens of an eye, the looped segment having a bottom portion configured to engage and sever a bottom portion of the lens upon moving toward the contracted configuration when the looped segment is placed around the lens,
a light-conducting element extending along at least a portion of a length of the looped segment, and
a light source in communication with the light-conducting element, such that light from the light source travels through the element and illuminates at least a portion of the length of the looped segment,
wherein the light-conducting element is a tube that surrounds the wire, and wherein the wire is bent in two places in opposite directions at the bottom portion of the looped segment, so as to create an intermediate section that is not parallel to the looped segment and extends toward the elongated shaft, and wherein the tube terminates at the intermediate section of the looped segment, so that a distal end of the tube is facing the elongated shaft.

2. The ophthalmic surgical instrument according to claim 1, wherein the light-conducting element is translucent.

3. The ophthalmic surgical instrument according to claim 1, wherein the light-conducting element is made of polyurethane.

4. The ophthalmic surgical instrument according to claim 1, wherein the light-conducting element is opaque, or covered by an opaque coating or covering, so that light from the light source is only visible at the distal end of the light-conducting element.

5. The ophthalmic surgical instrument according to claim 4, wherein the light-conducting element and wire are covered by a covering that is woven or coiled.

6. The ophthalmic surgical instrument according to claim 5, wherein the covering is made of metal.

7. The ophthalmic surgical instrument according to claim 1, wherein the wire is made of nitinol.

8. The ophthalmic surgical instrument according to claim 1, wherein the light-conducting element extends through the elongated shaft.

9. The ophthalmic surgical instrument according to claim 1, further comprising a housing connected to the elongated shaft, the housing comprising an actuator connected to the wire and being configured to move the wire between the contracted and dilated configurations.

10. The ophthalmic surgical instrument according to claim 9, wherein the light source is disposed in the housing.

11. The ophthalmic surgical instrument according to claim 9, wherein the light source is located external to the housing and wherein the tube extends through the housing to the light source.

12. The ophthalmic surgical instrument according to claim 9, wherein the actuator comprises a sliding element disposed in a slot in the housing.

13. The ophthalmic surgical instrument according to claim 9, wherein the light source is powered by a battery disposed in the housing.

14. The ophthalmic surgical instrument according to claim 1, wherein the light source is a light-emitting diode (LED).

* * * * *